US011147913B2

United States Patent
Azapagic et al.

(10) Patent No.: US 11,147,913 B2
(45) Date of Patent: Oct. 19, 2021

(54) PLATEN FOR PERISTALTIC INFUSION PUMP

(71) Applicant: Curlin Medical Inc., Elma, NY (US)

(72) Inventors: Azur Azapagic, Cottonwood Heights, UT (US); Daniel Martel, Stansbury Park, UT (US)

(73) Assignee: Curlin Medical Inc., Elma, NY (US)

( * ) Notice: Subject to any disclaimer, the term of this patent is extended or adjusted under 35 U.S.C. 154(b) by 189 days.

(21) Appl. No.: 16/211,536

(22) Filed: Dec. 6, 2018

(65) Prior Publication Data

US 2020/0179593 A1   Jun. 11, 2020

(51) Int. Cl.
*A61M 5/142* (2006.01)
*F04B 43/12* (2006.01)

(52) U.S. Cl.
CPC .... *A61M 5/14232* (2013.01); *A61M 5/14228* (2013.01); *F04B 43/1246* (2013.01)

(58) Field of Classification Search
CPC .......... A61M 5/14232; A61M 5/14228; A61M 5/142; F04B 43/12; F04B 43/1238; F04B 43/14246; F04B 43/1215; F04B 43/1223; F04B 43/1246; F04B 43/1253
See application file for complete search history.

(56) References Cited

U.S. PATENT DOCUMENTS

| | | | | |
|---|---|---|---|---|
| 6,164,921 A | * | 12/2000 | Moubayed | A61M 5/14228 417/44.1 |
| 6,371,732 B1 | * | 4/2002 | Moubayed | A61M 5/14228 417/44.1 |
| 6,629,955 B2 | * | 10/2003 | Morris | A61M 5/14228 604/153 |
| 2005/0025647 A1 | | 2/2005 | Ortega et al. | |
| 2014/0161635 A1 | * | 6/2014 | Momeni | F04B 43/082 417/53 |
| 2018/0050153 A1 | * | 2/2018 | Azapagic | G16H 40/63 |

* cited by examiner

*Primary Examiner* — Nathan R Price
*Assistant Examiner* — Tasnim Mehjabin Ahmed
(74) *Attorney, Agent, or Firm* — Hodgson Russ LLP

(57) ABSTRACT

A platen assembly positionable opposite a pumping mechanism of an infusion pump has a first platen member rotatably coupled to the pump to pivot about a first hinge axis and a second platen member rotatably coupled to the first platen member to pivot about a second hinge axis different from the first hinge axis. When the platen assembly is in a pump operating position, respective platen surfaces of the platen members follow a single surface profile, for example an arcuate surface profile in the case of a curvilinear peristaltic pump. The platen assembly may have a damage-tolerant design including a plurality of alignment counter-features arranged to mate with corresponding alignment features on the pump, wherein the platen assembly may still close after the pump is dropped or damaged only if resulting deformation of the platen assembly is within an allowable tolerance for safe pumping.

13 Claims, 5 Drawing Sheets

PLATEN FOR PERISTALTIC INFUSION PUMP

FIELD OF THE INVENTION

The present invention relates to a platen assembly for a peristaltic infusion pump.

BACKGROUND OF THE INVENTION

Programmable infusion pumps are used to carry out controlled delivery of liquid food for enteral feeding and medications for various purposes such as pain management. In a common arrangement, an infusion pump receives a disposable administration set comprising flexible tubing having a resiliently deformable tubing segment designed to be engaged by a pumping mechanism of the infusion pump. For example, the pumping mechanism may include a plurality of fingers sequentially driven against the tubing segment to locally deform the tubing segment in a peristaltic manner to force liquid through the tubing toward the patient. During pumping, a platen member of the infusion pump is held at a fixed position on a side of the tubing segment opposite from the pumping mechanism to provide a platen surface along the tubing segment for keeping the tubing segment in place against the pressure of the pumping mechanism. In prior art infusion pumps, the platen member of the pump is a one-piece member rotatably mounted on a body of the pump, whereby the platen member may be pivoted about a hinge axis between an open position and a closed position. In the open position, the platen member is pivoted away from the pump body to allow an administration set to be loaded in the infusion pump with the tubing segment adjacent the pumping mechanism. In the closed position, the platen member is pivoted toward the pump body and latched or locked with respect to the pump body such that the platen surface is held at an operating position adjacent to the tubing segment and opposite from the pumping mechanism. An example of the arrangement described above is disclosed in U.S. Pat. No. 6,164,921 to Moubayed et al.

It is recognized that infusion pumps are subject to damage which may affect pumping performance and patient safety. Infusion pumps, especially so-called "ambulatory" infusion pumps designed to be carried by a patient for daily use, may be dropped from time to time, whereby the platen member may be deformed. Depending upon the extent of deformation, undetectable free flow and/or uncontrolled or inaccurate fluid flow may occur, creating a safety risk that the patient may receive too much or too little infusion liquid relative to the prescribed amount. Prior art infusion pumps have no way of detecting and assessing platen damage, or making a decision as to whether the damage renders the infusion pump unsafe to use.

SUMMARY OF THE INVENTION

The present disclosure provides a damage-resistant and damage-tolerant platen assembly for an infusion pump. The platen assembly includes a first platen member rotatably coupled to a body of the infusion pump to pivot relative to the pump body about a first hinge axis and a second platen member rotatably coupled to the first platen member to pivot relative to the first platen member about a second hinge axis. The platen assembly is pivotable about the first hinge axis to an open position in which the second platen member and the first platen member are positioned away from a pumping mechanism in the pump body, and to a closed position in which the second platen member and the first platen member are positioned opposite and in proximity to the pumping mechanism for operation of the pump.

The first platen member may include a bend or a curve between the first hinge axis and the second hinge axis such that a load path through the first platen member from the second hinge axis to the first hinge axis is non-linear, thereby creating a moment about the first hinge axis to resist damage to the platen assembly if the pump is dropped.

The platen assembly may have a damage-tolerant design including a plurality of alignment counter-features arranged to mate with corresponding alignment features on the pump, wherein the platen assembly may still close after the pump is dropped or damaged only if resulting deformation of the platen assembly is within an allowable tolerance for safe pumping.

The first platen member may include a first platen surface and the second platen member may include a second platen surface, wherein the first platen surface and the second platen surface engage tubing of an administration set received by the infusion pump when the platen assembly is in the closed position. In the closed position of the platen assembly, the first and second platen surfaces may follow a single surface profile, for example an arcuate surface profile in the case of a curvilinear peristaltic pump.

The first platen member may include a mounting portion configured for rotatably mounting the first platen member on the pump body for rotation about the first hinge axis and a branch extending from the mounting portion. The mounting portion may be thicker than the branch in a direction of the first hinge axis, and the branch may be located between and spaced from opposite axial ends of the mounting portion, so that tubing of the administration set can enter the pump through a gap or opening immediately in front of the first platen member or through a gap or opening immediately to the rear of the first platen member.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
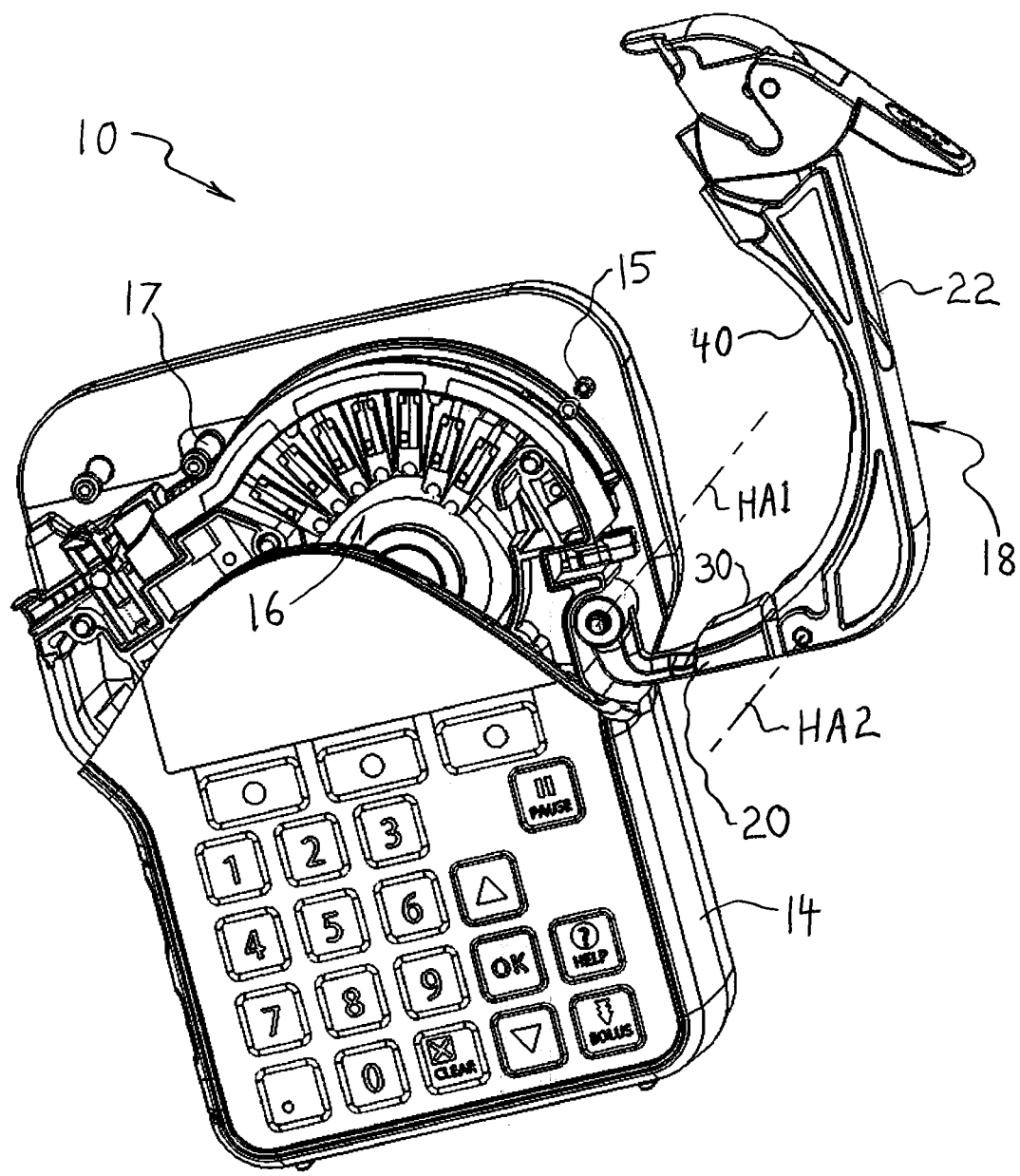
FIG. 1 is a perspective view showing an infusion pump formed in accordance with an embodiment of the present invention, wherein a platen assembly of the infusion pump is shown in an open position thereof.
Figure 2:
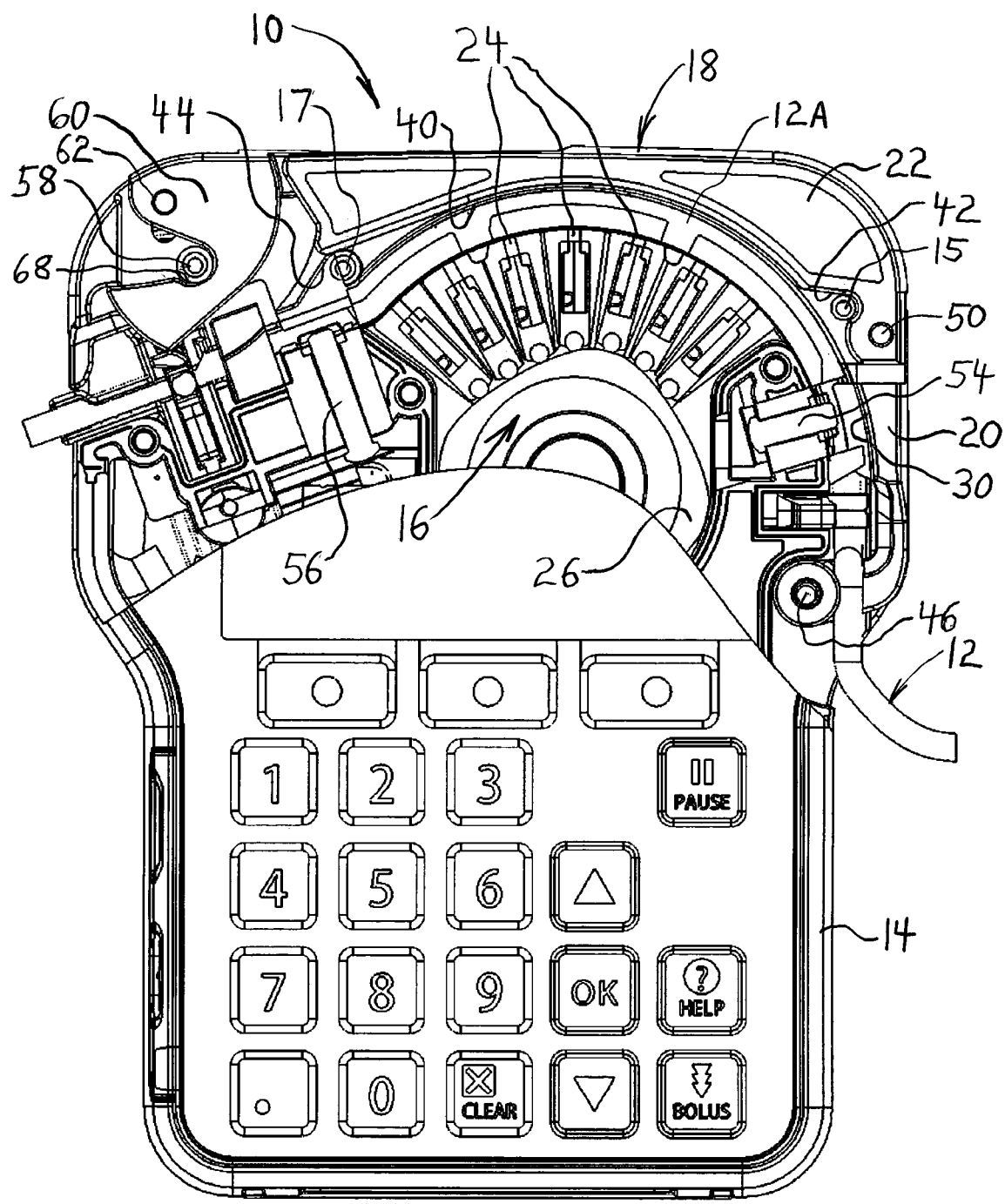
FIG. 2 is a front view of the infusion pump shown in FIG. 1, partially cutaway to show internal structure of the infusion pump, wherein the platen assembly is shown in a closed position thereof and an administration set is loaded in the infusion pump.

FIGS. 1 and 2 show an infusion pump 10 formed in accordance with a disclosed embodiment. In FIG. 1, infusion pump 10 is shown alone, whereas in FIG. 2, infusion pump 10 is shown with a disposable administration set 12 loaded in the pump, wherein administration set 12 is designed to be removably received by infusion pump 10. Administration set 12 includes flexible tubing acted upon by pump 10 to convey a flow of infusion liquid from a source reservoir (not shown) to a patient (not shown).

Infusion pump 10 comprises a pump body 14 including a pumping mechanism 16. Pump 10 also comprises a platen assembly 18 which includes a first platen member 20 rotatably coupled to pump body 14 to pivot relative to pump body 14 about a first hinge axis HA1 and a second platen member 22 rotatably coupled to first platen member 20 to pivot relative to first platen member 20 about a second hinge axis HA2. First hinge axis HA1 and second hinge axis HA2 may be parallel to one another. As shown in FIG. 1, platen assembly 18 is pivotable about first hinge axis HA1 to an open position in which second platen member 22 and first platen member 20 are positioned away from pumping mechanism 16. When platen assembly 18 is in the open position depicted in FIG. 1, pumping mechanism 16 is exposed, thereby allowing a disposable administration set 12 to be loaded into infusion pump 10 such that a tubing segment 12A of the administration set is adjacent to pumping mechanism 16. As may be understood from FIG. 2, platen assembly 18 is pivotable about first hinge axis HA1 to a closed position in which second platen member 22 and the first platen member 20 are positioned opposite and in proximity to pumping mechanism 16.

Pumping mechanism 16 may be a peristaltic pumping mechanism having a plurality of extendable and retractable pumping fingers 24 that are driven in sequential peristaltic fashion to engage and temporarily deform tubing segment 12A such that liquid is pumped through the tubing of administration set 12 in the direction of the patient. In the illustrated embodiment, pumping mechanism 16 has a curvilinear configuration, and pumping fingers 24 are moved generally radially by rotation of a motor-driven eccentric cam 26. Pumping mechanism 16 may take other forms, such as a linear peristaltic pumping mechanism having axially spaced fingers moved by respective cams mounted on a rotary shaft, or a rotary pumping mechanism having a motor-driven rotor about which tubing segment 12A is partially wound for engagement by pumping elements on the rotor.

Figure 3A:
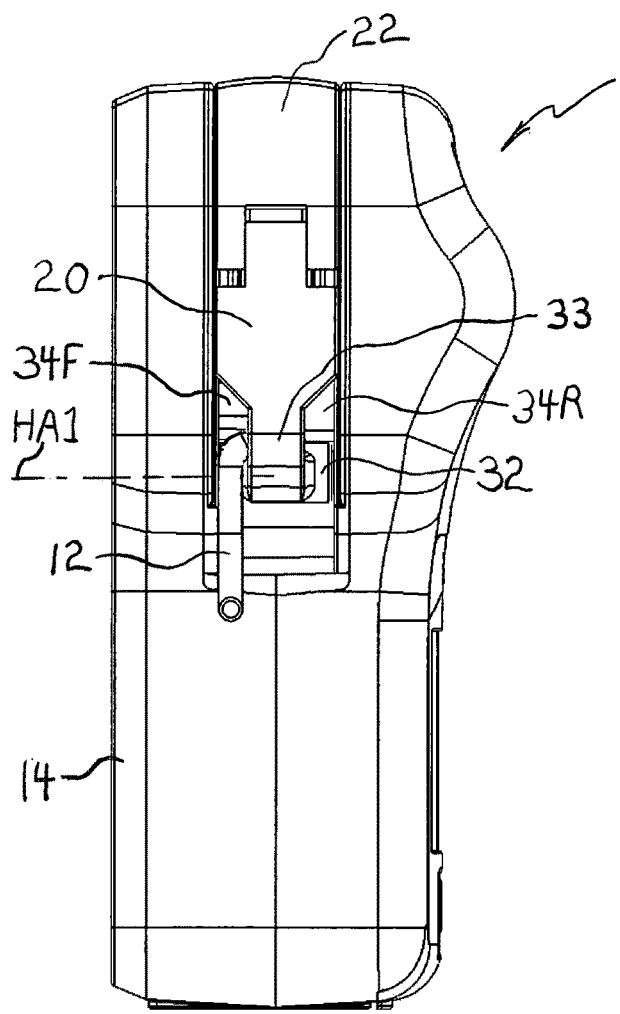
FIG. 3A is a side view of the infusion pump shown in FIGS. 1 and 2, wherein the platen assembly is shown in the closed position and an administration set is loaded in the infusion pump.
Figure 3B:
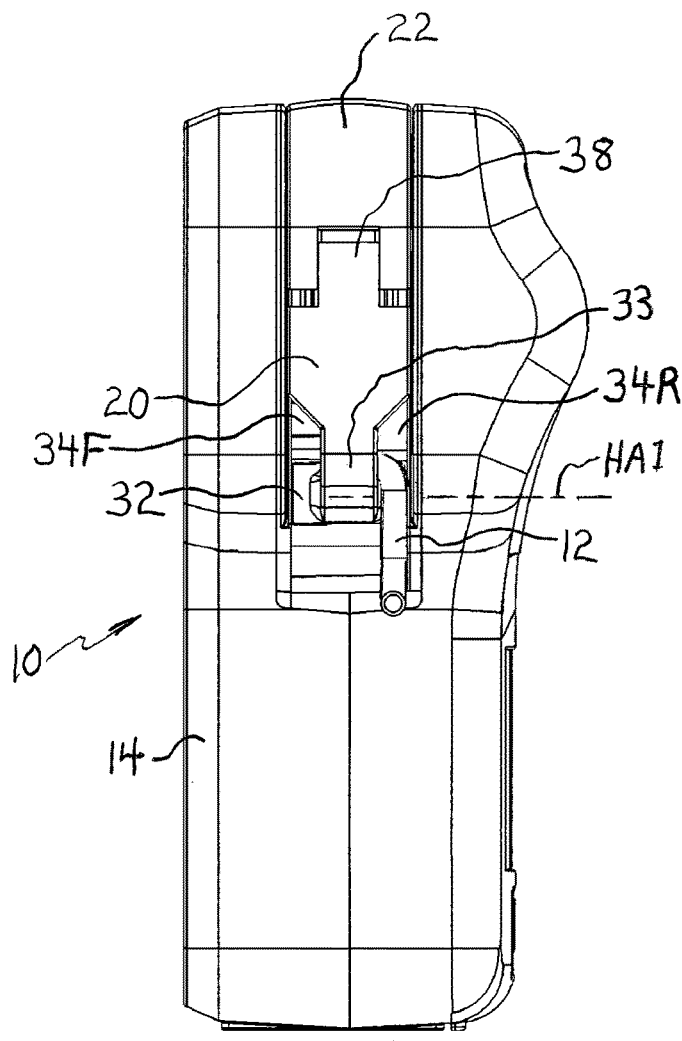
FIG. 3B is a side view of the infusion pump similar to that of FIG. 3A, shown an alternative arrangement of the loaded administration set.
Figure 4:
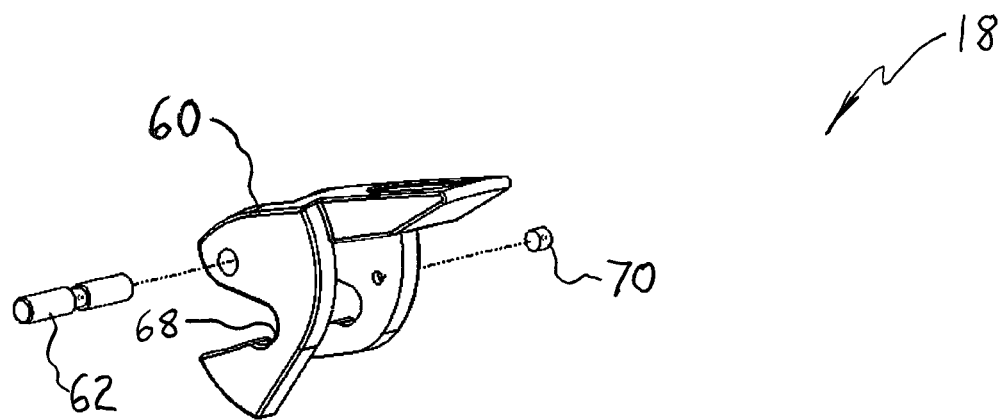
FIG. 4 is an exploded perspective view of the platen assembly.
Figure 4:
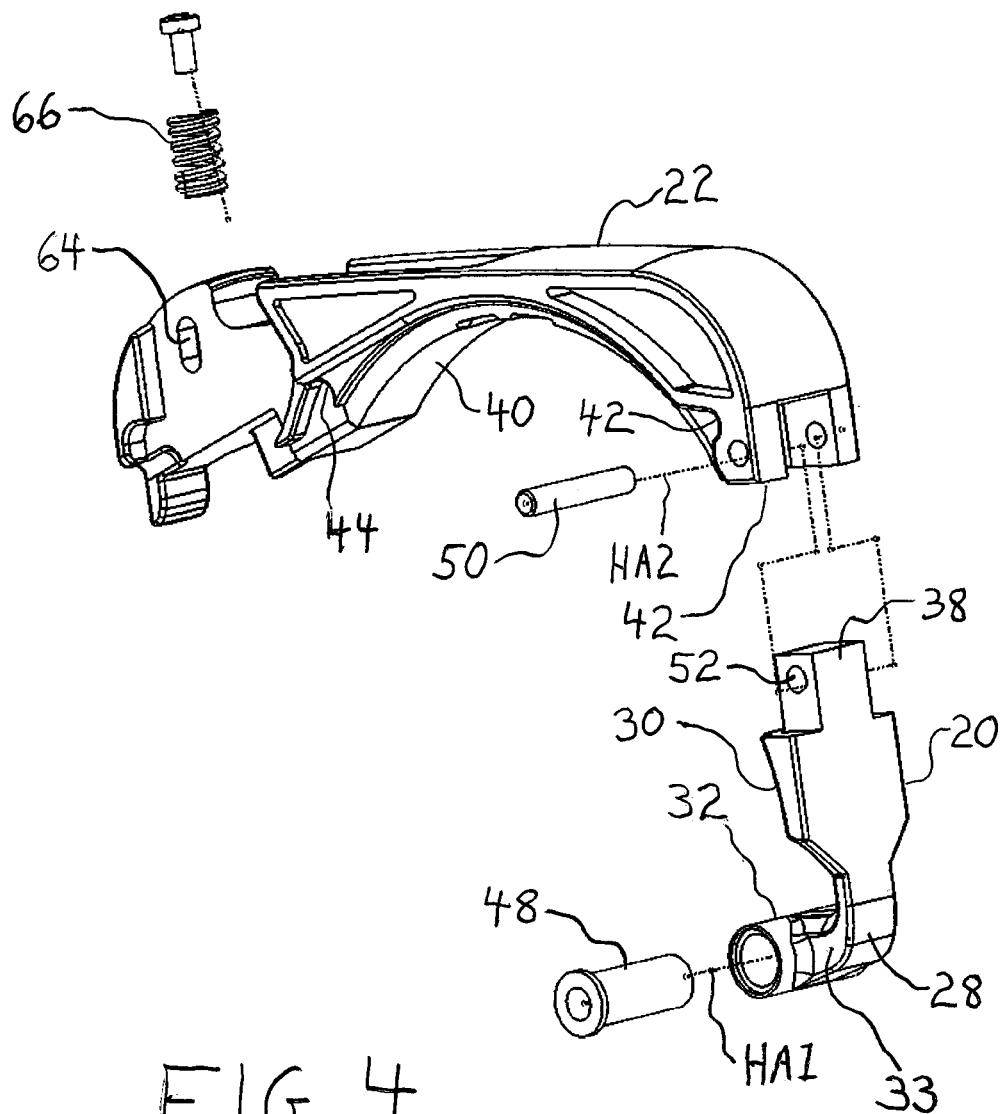

Platen assembly 18 is now further described with reference to FIGS. 3 and 4 in addition to FIGS. 1 and 2.

First platen member 20 may include a bend or a curve 28 between first hinge axis HA1 and second hinge axis HA2, whereby a direct linear load path between second hinge axis HA2 and first hinge axis HA1 is avoided. Such a configuration of first platen member 20 is advantageous because impact force imparted to second platen member 22 if pump 10 is dropped will result in a moment about first hinge axis HA1 to help resist damage to platen members 20, 22. First platen member 20 may include a first platen surface 30, which may be located between bend or curve 28 and second hinge axis HA2, wherein first platen surface 30 engages tubing segment 12A of administration set 12 when platen assembly 18 is in the closed position. First platen member 20 may include a mounting portion 32 configured for rotatably mounting first platen member 20 on pump body 14 for rotation about first hinge axis HA1 and a branch 33 extending from mounting portion 32. Mounting portion 32 may be thicker than branch 33 in a direction of first hinge axis HA1 and branch 33 may be located between and spaced from opposite axial ends of mounting portion 32, thereby providing both a front opening 34F in front of branch 33 and a rear opening 34R behind branch 33 for tubing of administration set 12 to enter pump 10. As a result, the user may load the tubing such that the tubing extends either through front opening 34F as shown in FIG. 3A or through rear opening 34R as shown in FIG. 3B because both of these arrangements are intended and correct. Branch 33 may be centrally located between the opposite axial ends of mounting portion 32 to define two equal openings 34F and 34R. First platen member 20 may have a distal end 38 configured for rotatable coupling of second platen member 22 thereto.

Second platen member 22 may be arranged and sized to extend over pumping fingers 24 of pumping mechanism 16 when platen assembly 18 is in the closed position such that a second platen surface 40 provided on second platen member 22 engages tubing segment 12A. Second platen member 22 may be configured to have a clevis-shaped end 42 for receiving distal end 38 of first platen member 20.

Platen assembly 18 may include a plurality of alignment counter-features 42, 44 for respectively mating with a plurality of alignment features 15, 17 provided on pump body 14, whereby movement of platen assembly 18 to the closed position will be prevented if platen assembly 18 is deformed beyond a predetermined tolerance limit, as may occur for instance if pump 10 is accidentally dropped. In the illustrated embodiment shown, alignment counter-features 42, 44 are provided on second platen member 22. First alignment counter-feature 42 may be located adjacent to a proximal end of second platen surface 40, and second alignment counter-feature 44 may be located adjacent to an opposite distal end of second platen surface 40. Mating of first alignment feature 15 with first alignment counter-feature 42, and mating of second alignment feature 17 with second alignment counter-feature 44, occurs when platen assembly 18 is pivoted about first hinge axis HA1 to its closed position. By providing multiple alignment features 15, 17 on pump body 14 and corresponding counter-features 42, 44 on second platen member 22, and by locating an alignment feature and corresponding alignment counter-feature adjacent to each opposite end of second platen surface 40, safety-critical positioning of second platen surface 40 with respect to tubing segment 12A is confirmed upon closure of platen assembly 18. The alignment features 15, 17 may be embodied as pins and the alignment counter-features 42, 44 may be embodied as slots in accordance with the drawing figures. Alternatively, the alignment features 15, 17 may be embodied as slots and the alignment counter-features 42, 44 may be embodied as pins, or the alignment features 15, 17 may include at least one pin and at least one slot and the counter-features 42, 44 may include at least one slot and at least one pin.

The manner by which first platen member 20 may be rotatably coupled to pump body 14 may vary. In one example, first platen member 20 may be rotatably coupled to pump body 14 by a pivot pin 46 mounted on pump body 14 and arranged to extend through a cylindrical bushing 48 provided in mounting portion 32 of first platen member 20. Likewise, the manner by which second platen member 22 may be rotatably coupled to first platen member 20 is subject to variation. By way of example, a pivot pin 50 provided at clevis-shaped end 42 of second platen member 22 and arranged to extend through a hole 52 in mating distal end 38 of first platen member 20. Of course, other arrangements for rotatably coupling first platen member 20 to pump body 14, and second platen member 22 to first platen member 20, may be used.

As mentioned above, pumping mechanism 16 may have a curvilinear configuration, wherein pumping fingers 24 are moved generally radially. In this case, first platen surface 30 associated with first platen member 20 and second platen surface 40 associated with second platen member 22 may be arcuate platen surfaces configured to follow a single arcuate profile when platen assembly 18 is in the closed position, as may be seen in FIG. 2. In the closed position, second platen surface 40 may oppose all the pumping fingers 24, and first platen surface 30 may oppose an upstream pressure sensor as described below. It is also possible to reconfigure platen assembly 18 such that some of the pumping fingers 24 are opposed by first platen surface 30.

Infusion pump 10 may comprise an upstream pressure sensor 54 and a downstream pressure sensor 56 arranged to detect fluid pressure within tubing segment 12A of administration set 12 at locations upstream and downstream from pumping mechanism 16, respectively. Upstream pressure sensor 54 may be arranged to detect fluid pressure at a location opposite from first platen surface 30, and downstream pressure sensor 56 may be arranged to detect fluid pressure at a location opposite from second platen surface 40. This arrangement has the advantage that upstream pressure sensor 54 may be used to detect a pressure drift if first platen member 20 is deformed beyond an allowable tolerance, and downstream pressure sensor 56 may be used to independently detect a pressure drift if second platen member 22 is deformed beyond an allowable tolerance. By way of example, pressure sensors 54, 56 may each include a plunger having one end arranged to engage an outer surface of tubing segment 12A and an opposite end arranged to engage a strain beam transducer, wherein expansion and contraction of the tubing segment due to fluid pressure changes is transmitted to the strain beam transducer to generate a corresponding voltage signal representing fluid pressure at the location where the plunger contacts the tubing segment.

To secure platen assembly 18 in its closed position for pumping operation after administration set 12 is loaded in the pump, platen assembly 18 may include a latch member 60 for engaging a latching feature 58 on pump body 14. Latch member 60 may be rotatably coupled to second platen member 22 by a pivot pin 62. Pivot pin 62 may be arranged to extend through a slightly elongated passage 64 proceeding transversely through second platen member 22, and a spring 66 may be arranged to bias pivot pin 62 toward an upper end of passage 64. Latch member 60 may be provided with a latching counter-feature 68 arranged and configured such that when platen assembly 18 is in the closed position and latch member 60 is pivoted in a clockwise direction as viewed in FIGS. 1 and 2, latching counter-feature 68 will engage with latching feature 58 in a cam-like manner to progressively pull the end of second platen member 22 downward relative to latch member 60 against the bias of spring 66 until latching feature 58 is received at an inner end region of latching counter-feature 68, at which point second platen member 22 is forced in an upward direction relative to latch member 60 by spring 66 to securely hold latching feature 58 in engagement with latching counter-feature 68 in spring-biased fashion, thereby locking platen assembly 18 in its proper static position opposite pumping mechanism 16. Latch member 60 may include a magnet 70 detectable by a latch sensor 72 (see FIG. 5) housed in or on pump body 14 to generate a latching signal indicative of whether or not platen assembly 18 is properly latched. For example, latch sensor 72 may be a Hall effect sensor.

When platen assembly 18 is properly closed and latched, second platen surface 40 of second platen member 22 may interact with pumping fingers 24 to create a peristaltic pumping of fluid through tubing segment 12A. Second platen member 22 including second platen surface 40 is located and locked in a specific static position to ensure controlled and accurate delivery of fluid. As mentioned above, second platen surface 40 may be curved around pumping fingers 24, and tubing segment 12A may be located between second platen surface 40 and pumping fingers 24. Alignment features 15, 17 and alignment counter-features 42, 44 may be configured and arranged to mate even if platen assembly 18 is damaged or deformed, so long as the damage or deformation of platen assembly 18 is within an allowable tolerance for which controlled and accurate delivery of fluid is maintained. If platen assembly 18 is damaged or deformed beyond the allowable tolerance, then alignment features 15, 17 will not properly mate with alignment counter-features 42, 44, and pump 10 may be disabled to prevent a user from using the pump in an unsafe condition.

In the illustrated embodiment, first platen member 20 is configured and arranged to absorb and/or divert impact energy if pump 10 is dropped, thereby protecting the structural integrity of second platen member 22. Impact energy may be transmitted from second platen member 22 to first platen member 20 through the coupling at second hinge axis HA2, however some of the impact energy will be diverted to cause rotational displacement between first platen member 20 and second platen member 22 about second hinge axis HA2, and rotational displacement between first platen member 20 and pump body 14 about first hinge axis HA1. Impact energy not diverted to cause rotational displacement may be absorbed by first platen member 20 through deformation. As may be understood, rotational displacement and/or deformation of first platen member 20 resulting from compression force at impact can only result in a shortening of the distance between pivot pins 46 and 50 (to make this distance longer it is necessary to apply a high tension stress, which is not possible from dropping pump 10). Any change in the position of second platen member 22 from dropping pump 10 will always have a downward component toward pumping mechanism 16 rather than an upward component away from pumping mechanism 16. Because upward displacement of second platen member 22 and second platen surface 40 away from pumping mechanism 16 may cause a dangerous free-flow condition, the disclosed platen assembly 18 reduces safety risk associated with dropping pump 10.

Figure 5:
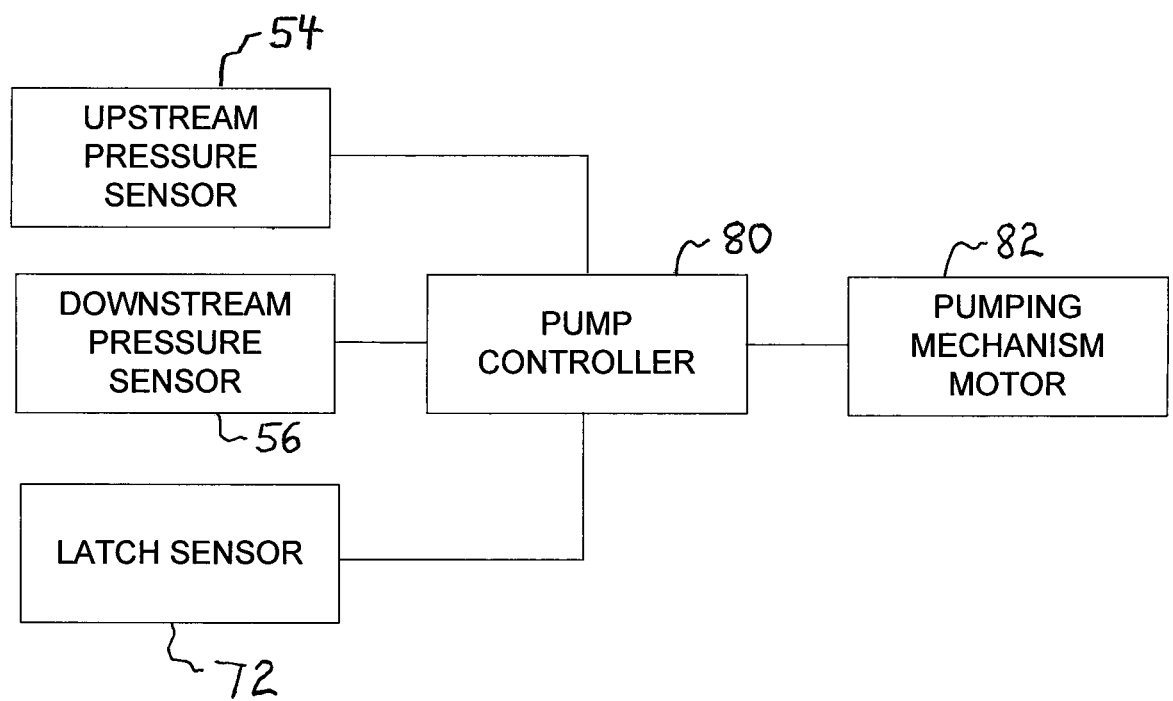
FIG. 5 is a schematic block diagram of electronic circuitry of the infusion pump shown in FIGS. 1 and 2.

Reference is now made to FIG. 5. In another aspect of the present disclosure, signals generated by upstream pressure sensor 54, downstream pressure sensor 56, and latch sensor 72 may be provided to a pump controller 80 which controls a drive motor 82 of pumping mechanism 16. The respective signals may be evaluated by control logic programmed into memory associated with pump controller 80 to disable the motor 82 of pumping mechanism 16 and thereby prevent pump operation if the upstream pressure signal from upstream pressure sensor 54 is not within predetermined limits as expected, if the downstream pressure signal from downstream pressure sensor 56 is not within predetermined limits as expected, or if the latching signal from latch sensor 72 indicates that platen assembly 18 is not properly latched. Thus, if platen assembly 18 is still able to be physically latched after pump 10 has been dropped, but there is some deformation in the platen assembly that disturbs the location of first platen surface 30 and/or second platen surface 40 relative to pumping mechanism 16 and causes pressure drift, this condition can be sensed prior to pumping and corrective action can be taken.

While the present disclosure describes exemplary embodiments, the detailed description is not intended to limit the scope of the invention to the particular forms set forth. The invention is intended to cover such alternatives, modifications and equivalents of the described embodiments as may be included within the scope of the claims.

What is claimed is:

1. An infusion pump comprising:
a pump body including a pumping mechanism;
a platen assembly including a first platen member rotatably coupled to the pump body to pivot relative to the pump body about a first hinge axis and a second platen member rotatably coupled to the first platen member to pivot relative to the first platen member about a second hinge axis, wherein the first hinge axis and the second hinge axis are parallel to one another;
wherein the platen assembly further includes a first platen surface on the first platen member and a second platen surface on the second platen member;
wherein the platen assembly is pivotable about the first hinge axis to an open position in which the second platen surface and the first platen surface are positioned away from the pumping mechanism;
wherein the platen assembly is pivotable about the first hinge axis to a closed position in which the second platen surface and the first platen surface are positioned opposite and in proximity to the pumping mechanism and wherein the first platen surface and the second platen surface engage tubing of an administration set received by the infusion pump.

2. The infusion pump according to claim 1, wherein the first platen member includes a bend or a curve between the first hinge axis and the second hinge axis.

3. The infusion pump according to claim 1, wherein the pump body includes a first alignment feature and a second alignment feature, the platen assembly includes a first alignment counter-feature and a second alignment counter-feature, and the first alignment feature and second alignment feature respectively mate with the first alignment counter-feature and the second alignment counter-feature when the platen assembly is in the closed position.

4. The infusion pump according to claim 3, wherein the first alignment counter-feature and the second alignment counter-feature are included on the second platen member.

5. The infusion pump according to claim 3, wherein the first alignment feature includes a first pin and the first alignment counter-feature includes a first slot.

6. The infusion pump according to claim 5, wherein the second alignment feature includes a second pin, and the second alignment counter-feature includes a slot different from the first slot.

7. The infusion pump according to claim 1, further comprising an upstream pressure sensor and a downstream pressure sensor, wherein the upstream pressure sensor is arranged to detect pressure within tubing of the administration set received by the infusion pump at a location opposite from the first platen surface and the downstream pressure sensor is arranged to detect pressure within the tubing of the administration set at a location opposite from the second platen surface.

8. An infusion pump comprising:
a pump body including a pumping mechanism;
a platen assembly including a first platen member rotatably coupled to the pump body to pivot relative to the pump body about a first hinge axis and a second platen member rotatably coupled to the first platen member to pivot relative to the first platen member about a second hinge axis;
wherein the platen assembly further includes a first platen surface on the first platen member and a second platen surface on the second platen member;
wherein the platen assembly is pivotable about the first hinge axis to an open position in which the second platen surface and the first platen surface are positioned away from the pumping mechanism;
wherein the platen assembly is pivotable about the first hinge axis to a closed position in which the second platen surface and the first platen surface are positioned opposite and in proximity to the pumping mechanism and wherein the first platen surface and the second platen surface engage tubing of an administration set received by the infusion pump;
wherein the pump body includes a first alignment feature and a second alignment feature, the platen assembly includes a first alignment counter-feature and a second alignment counter-feature, and the first alignment feature and second alignment feature respectively mate with the first alignment counter-feature and the second alignment counter-feature when the platen assembly is in the closed position;
wherein the first alignment counter-feature and the second alignment counter-feature are included on the second platen member;
wherein the first alignment counter-feature and the second alignment counter-feature are respectively located adjacent to opposite ends of the second platen surface.

9. An infusion pump comprising:
a pump body including a pumping mechanism;
a platen assembly including a first platen member rotatably coupled to the pump body to pivot relative to the pump body about a first hinge axis and a second platen member rotatably coupled to the first platen member to pivot relative to the first platen member about a second hinge axis;
wherein the platen assembly further includes a first platen surface on the first platen member and a second platen surface on the second platen member;
wherein the platen assembly is pivotable about the first hinge axis to an open position in which the second platen surface and the first platen surface are positioned away from the pumping mechanism;
wherein the platen assembly is pivotable about the first hinge axis to a closed position in which the second platen surface and the first platen surface are positioned opposite and in proximity to the pumping mechanism and wherein the first platen surface and the second platen surface engage tubing of an administration set received by the infusion pump;
wherein the first platen member includes a mounting portion configured for rotatably mounting the first platen member on the pump body for rotation about the first hinge axis and a branch extending from the mounting portion, wherein the mounting portion is thicker than the branch in a direction of the first hinge axis, and the branch is located between and spaced from opposite axial ends of the mounting portion.

10. The infusion pump according to claim 9, wherein the branch is centrally located between the opposite axial ends of the mounting portion.

11. An infusion pump comprising:
a pump body including a pumping mechanism;

a platen assembly including a first platen member rotatably coupled to the pump body to pivot relative to the pump body about a first hinge axis and a second platen member rotatably coupled to the first platen member to pivot relative to the first platen member about a second hinge axis;

wherein the platen assembly further includes a first platen surface on the first platen member and a second platen surface on the second platen member;

wherein the platen assembly is pivotable about the first hinge axis to an open position in which the second platen surface and the first platen surface are positioned away from the pumping mechanism;

wherein the platen assembly is pivotable about the first hinge axis to a closed position in which the second platen surface and the first platen surface are positioned opposite and in proximity to the pumping mechanism and wherein the first platen surface and the second platen surface engage tubing of an administration set received by the infusion pump;

wherein the first platen surface includes a first arcuate platen surface and the second platen surface includes a second arcuate platen surface, and the first arcuate platen surface and the second arcuate platen surface follow a single arcuate profile when the platen assembly is in the closed position.

12. A platen assembly for an infusion pump, the platen assembly comprising:
   a first platen member having a first platen surface, the first platen member being rotatably coupled to the infusion pump to pivot relative to the infusion pump about a first hinge axis; and
   a second platen member having a second platen surface, the second platen member being rotatably coupled to the first platen member to pivot relative to the first platen member about a second hinge axis different from the first hinge axis, wherein the first hinge axis and the second hinge axis are parallel to one another;
   wherein the second platen member is pivotable relative to the first platen member to a pump operating position in which the first platen surface and the second platen surface follow a single surface profile, wherein the single surface profile is an arcuate surface profile.

13. The platen assembly according to claim 12, wherein the first platen member is configured such that a load path through the first platen member from the second hinge axis to the first hinge axis is non-linear.

\* \* \* \* \*